(12) United States Patent
Bowe et al.

(10) Patent No.: US 6,960,256 B2
(45) Date of Patent: Nov. 1, 2005

(54) FORMATION OF SMALL CRYSTALS

(75) Inventors: Michael Joseph Bowe, Preston (GB); John William Stairmand, Chester (GB); Linda Jane McCausland, Abingdon (GB)

(73) Assignee: Accentus plc, Didcot (GB)

( * ) Notice: Subject to any disclaimer, the term of this patent is extended or adjusted under 35 U.S.C. 154(b) by 0 days.

(21) Appl. No.: 10/476,156

(22) PCT Filed: May 2, 2002

(86) PCT No.: PCT/GB02/02006
§ 371 (c)(1),
(2), (4) Date: Oct. 27, 2003

(87) PCT Pub. No.: WO02/089942
PCT Pub. Date: Nov. 14, 2002

(65) Prior Publication Data
US 2004/0139908 A1 Jul. 22, 2004

(30) Foreign Application Priority Data
May 5, 2001 (GB) .............................................. 0111083
Nov. 15, 2001 (GB) ............................................. 0127380

(51) Int. Cl.[7] .............................................. C30B 7/08
(52) U.S. Cl. .................. 117/68; 117/69; 422/245.1; 23/293 R
(58) Field of Search .......................... 422/245.1; 117/68, 117/69; 23/293 R

(56) References Cited

U.S. PATENT DOCUMENTS

| | | | |
|---|---|---|---|
| 3,979,269 A | 9/1976 | Vassilev | ................. 204/158 S |
| 5,707,634 A | 1/1998 | Schmitt | ...................... 424/400 |

FOREIGN PATENT DOCUMENTS

| | | |
|---|---|---|
| GB | 2242376 | 10/1991 |
| WO | 96/32095 | 10/1996 |
| WO | 00/44468 | 8/2000 |

Primary Examiner—Robert Kunemund
(74) Attorney, Agent, or Firm—William H. Holt

(57) ABSTRACT

Small crystals are made by mixing a solution of a desired substance with an anti-solvent in a fluidic vortex mixer in which the residence time is less than 1 s, for example 10 ms. The liquid within the fluidic vortex mixer (12) is subjected to high intensity ultrasound from a transducer (20, 22) in or on the wall of the mixer, or coupled to a pipe supplying liquid to the mixer. The solution very rapidly becomes supersaturated, and the ultrasound can induce a very large number of nuclei for crystal growth. Small crystals, for example less than 5 μm, are formed that may be of a suitable size for use in inhalers.

12 Claims, 4 Drawing Sheets

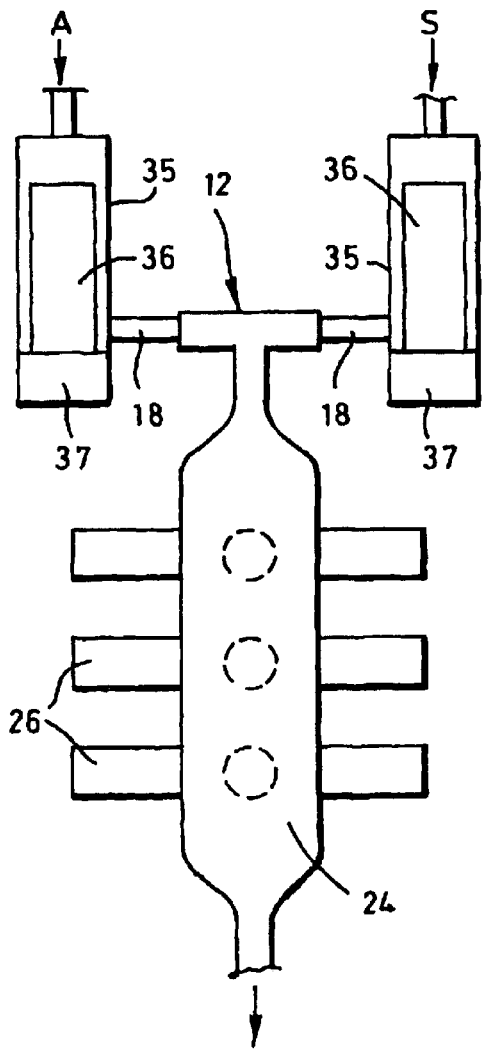
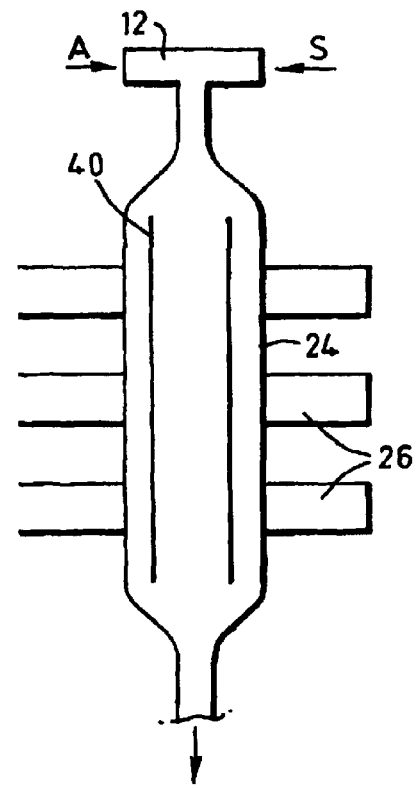
Fig.4.
Fig.5.

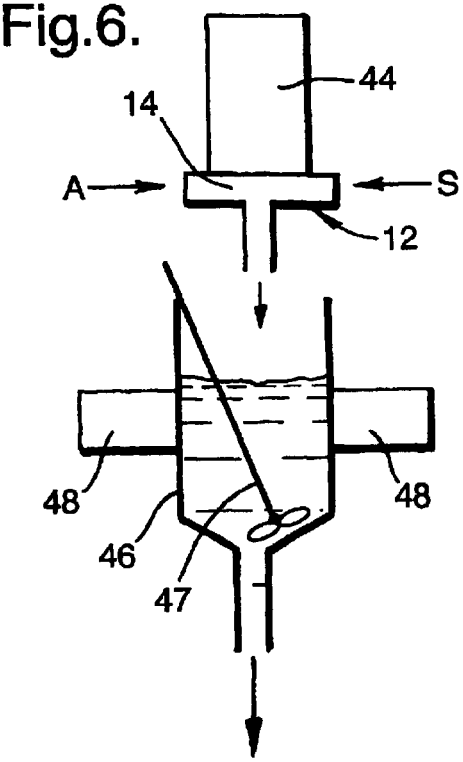
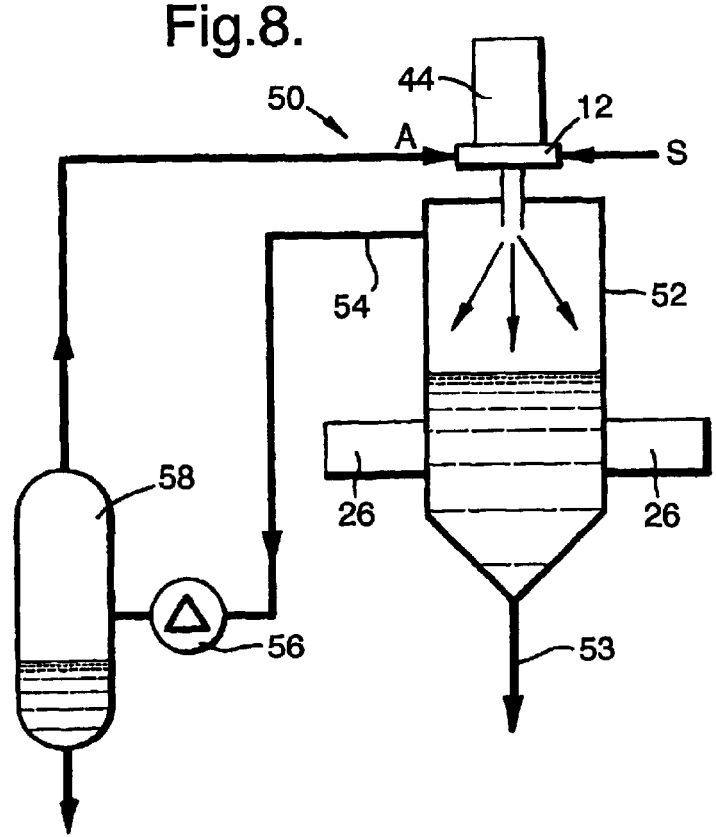

FORMATION OF SMALL CRYSTALS

This invention relates to an apparatus and a process for making small crystals, preferably but not exclusively crystals of size less than 10 μm.

The control of crystal and precipitate particle size and morphology is very important in some circumstances, in particular in the pharmaceutical and agro-chemical industries in which the final product form is a fine powder. The way in which an active ingredient behaves, whether in the body or upon the surface of a leaf for example, depends critically upon the particle size of the product, and the particular crystal form. Small particles may be made by processes such as milling, but such processes may have a detrimental effect on the material properties and may also produce a significant proportion of particles which are too small for the desired use, so that crystallisation of crystals in the desired size range directly from a solution would be desirable.

For many years it has been known to bring about crystallisation by mixing a solvent containing a product to be crystallised with an anti-solvent, so that after mixing the solution is supersaturated and crystallisation occurs. GB 2 341 120 A describes a system in which the mixing utilizes a fluidic vortex mixer, and in which the emerging mixture is supplied directly to a precipitate entrapment device. The term anti-solvent means a fluid which promotes precipitation from the solvent of the product (or of a precursor for the product). The anti-solvent may comprise a cold gas, or a fluid which promotes the precipitation via a chemical reaction, or which decreases the solubility of the product in the solvent; it may be the same liquid as the solvent but at a different temperature, or it may be a different liquid from the solvent. EP 0 449 454 A (=GB 2 242 376) describes a system for bringing about on-line precipitation in which liquid reagents are thoroughly mixed using a fluidic vortex mixer, the mixture then being passed through a vessel comprising linked vortex cells in which a pulsed flow ensures a well-defined residence time, hence ensuring particles of a selected mean size are created. The benefits of applying intense ultrasound during a crystallisation process have also been recognized, for example as described in an article by Chris Price in Pharmaceutical Technology Europe, October 1997, as such insonation can be used to initiate nucleation, so overcoming the problems that can arise from supersaturation. WO 00/38811 indicates that rapid precipitation, for example by mixing a solution with an anti-solvent, is difficult to control; they describe a process for preparing crystalline particles in which liquids are mixed in a continuous flow cell in the presence of ultrasonic radiation. The flow cell is substantially cylindrical, with diametrically opposed inlets near the base, and one or more outlet ports at different heights above the base (giving different residence times and hence different particle sizes), the liquid being mixed by stirring and preferably without inducing any vortex effects.

Surprisingly, it has now being found that very desirable results can be obtained by applying insonation while mixing a solution of a desired substance with an anti-solvent in a fluidic vortex mixer in which the residence time is less than 1 s. Accordingly, the present invention provides a method of performing crystallization in which fluids are mixed to cause precipitation or crystallisation by passage through a fluidic vortex mixer, in which the fluids within the fluidic vortex mixer are subjected to high intensity ultrasound.

A fluidic vortex mixer comprises a vortex chamber with two or more peripheral inlets, at least one of which is substantially tangential, and with an axial outlet. Such a device can achieve very rapid and thorough mixing in a very short space of time; for example the residence time in the mixer may be less than 0.5 s, or even less than 0.1 s, for example 20 ms or 10 ms, though usually at least 1 ms. The chamber is substantially cylindrical, and contains no baffles to disrupt the vortex flow. Such a fluidic mixer can therefore achieve a very high degree of supersaturation when mixing a saturated solution with an antisolvent, because of the rapid and very thorough mixing.

If a liquid is subjected to an ultrasonic intensity above about 0.3 $W/cm^2$, then there is a significant deposition of energy into the liquid through attenuation and non-linear effects. This can be associated with cavitation, in which small bubbles are created which are filled with vapour or gas, and which collapse rapidly during the compression half-cycle of the ultrasonic wave. Cavitation may lead to temperature transients, and pressure transients, and can enhance the rate of crystallisation by enhancing nucleation. Indeed, the effects of such high intensity ultrasound may be referred to as sonochemistry, or more specifically as sonocrystallisation.

Hence, when mixing a saturated solution with an antisolvent, the solution rapidly becomes highly supersaturated and the ultrasound can induce a very large number of nuclei for crystal growth. Not only does the high intensity ultrasound induce nucleation in the supersaturated liquid created by the fluidic vortex mixer, but it also can be expected to suppress the formation of agglomerates of small crystals, and also to inhibit or eliminate fouling of the surfaces of the mixer and adjacent ducts by crystal growth on those surfaces. Hence this process can enable crystals of a material to be formed which are less than 10 μm in size, for example less than 5 μm or less than 1 μm. Such small crystals may be of a suitable size for use in inhalers.

The ultrasound may be supplied by a probe extending into the vortex chamber of the fluidic vortex mixer so as to ensure that the entire volume of the vortex chamber is insonated with ultrasound. Alternatively an ultrasonic transducer may be coupled to a wall of the vortex chamber so that ultrasound is transmitted through the wall into the vortex chamber. And in another alternative, ultrasonic transducers may be arranged to subject the liquid streams supplied to the vortex mixer, or the liquid mixture emerging from the vortex mixer, to ultrasonic insonation in such a way that ultrasound propagates through the liquids and pipes carrying those liquids into the vortex mixer. In addition, ultrasonic transducers may be arranged to subject the mixture emerging from the fluidic vortex mixer to intense ultrasonic insonation.

To ensure that the crystal size distribution is not significantly altered by crystal ripening after the crystals leave the mixer it may be desirable to generate a spray of small droplets each containing a single crystal at the outlet of the vortex mixer. This may be aided by introducing a gas such as air, nitrogen or argon into the fluidic mixer to be mixed with the other fluids. Such a spray of droplets can be dried (as in a spray dryer).

The beneficial results obtainable with a fluidic vortex mixer may also be obtainable with other rapid-mixing devices that have no moving parts, such as opposed jet mixers and Y-junction mixers.

The invention will now be further and more particularly described, by way of example only, and with reference to the accompanying drawings, in which:

FIG. 4 shows another modification to the apparatus of FIG. 1;

FIG. 5 shows a modification to the apparatus of FIG. 4;

FIG. 6 shows a modification to the apparatus of FIG. 1;

FIG. 8 shows a crystallisation apparatus incorporating modifications to the apparatus of FIG. 6.

Figure 1:
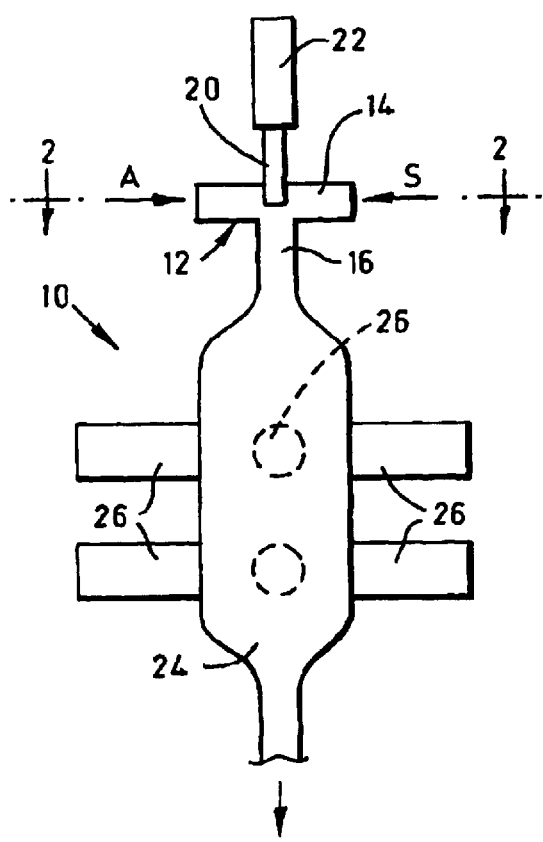
FIG. 1 shows a longitudinal sectional view of a crystallisation apparatus.
Figure 2:
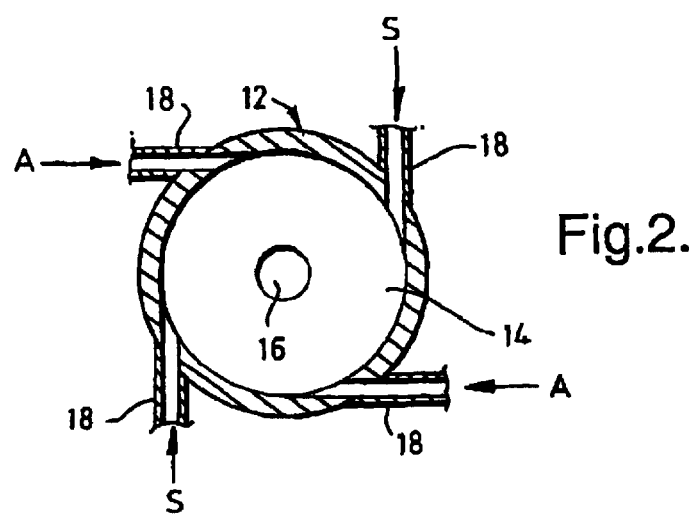
FIG. 2 shows a transverse sectional view on the line 2—2 of FIG. 1.

Referring now to FIG. 1, a crystallisation apparatus 10 comprises a vortex mixer 12 including a cylindrical chamber 14 of diameter 15 mm with an axial outlet 16 at the centre of an end wall, and with four tangential inlets 18 (only two of which are shown in FIG. 1) around its periphery. A saturated solution S of a desired substance is supplied to two inlets 18, and an anti-solvent A is supplied to the alternate two inlets, as indicated in FIG. 2. An ultrasonic probe 20 is mounted at the centre of the other end wall and projects into the middle of the chamber 14, its other end being connected to a 300 kHz transducer 22, so the position on the probe 20 at which it is sealed to the wall is a node when the transducer 22 is energised. The outlet 16 communicates with a product receiver vessel 24, an array of 20 kHz ultrasonic transducers 26 being mounted on the outside of the wall of the vessel 24.

Thus in use of the apparatus 10, the saturated solution S is thoroughly and rapidly mixed with the anti-solvent A, the volume of the chamber 14 and the flow rates being such that the residence time in the chamber 14 is for example 10 ms. The ultrasonic energy from the probe 20 insonates the entire volume of the chamber 14 with sufficient intensity to cause nucleation, as localized cavitation occurring on a microscopic scale promotes changes in fluid temperature and pressure that induce nucleation (and also promote formation of the most stable polymorph). By adjusting the power of the ultrasound, and the residence time in the chamber 14, the degree of nucleation can therefore be controlled. The ultrasound has the additional benefit that any crystal deposits within the chamber 14 tend to be removed from the surfaces. Within the receiver vessel 24 the crystal growth process is completed, the ultrasound from the transducers 26 breaking up any crystal agglomerations and preventing surface fouling.

It will be appreciated that the solvent in the solution S and the anti-solvent A must be selected as suitable for a particular substance. Preferably they are miscible with each other. As examples, in some cases the solvent might be acetone, and the anti-solvent be water; or the solvent might be methanol and the anti-solvent be water; or the solvent might be dimethyl formamide and the anti-solvent be water. The selection of appropriate solvent and anti-solvents must be made in accordance with the substance to be crystallised.

Figure 3:
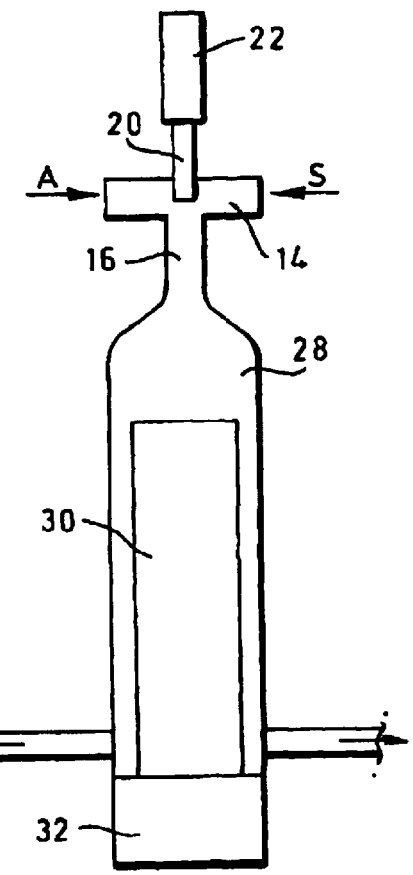
FIG. 3 shows a modification to the apparatus of FIG. 1.

Referring to FIG. 3, in a modification to the apparatus 10 the product receiver vessel is a flow-through ultrasound cell 28 with an ultrasonic probe 30 mounted internally, concentrically within the cell 28, coupled to a transducer 32 outside the cell 28.

Referring now to FIG. 4, in another modification to the apparatus 10 there is no ultrasonic transducer in or on the vortex mixer 12, and the product receiver vessel 24 is slightly larger than that shown in FIG. 1 and so has more transducers 26. Each of the pipes 18 carrying the solution S and the anti-solvent A into the vortex mixer 12 incorporates a respective ultrasonic flow-through cell 35 with an ultrasonic probe 36 mounted concentrically within the cell 35 and coupled to a transducer 37 outside the cell 35. This operates in substantially the same way as the apparatus of FIG. 1, in that the ultrasound from the probes 36 propagates through the pipes 18 into the vortex mixer 12 where it promotes nucleation and reduces fouling. The arrangement provides plug flow conditions which controls residence time to provide a further control on crystal growth and particle size.

Referring now to FIG. 5 there is shown a modification to the apparatus of FIG. 4 (that would be equally applicable to the apparatus 10 of FIG. 1), the modification being that the product receiver vessel 24 is provided with a draft tube 40, that is to say a concentric open-ended tube within the vessel 24. The outflow from the vortex mixer 12 causes liquid to flow downwardly through the draft tube 40, and there is a consequential recirculation with liquid flowing upwardly outside the draft tube 40. The ultrasonic transducers 26 subject the recirculating liquid to intense ultrasound, so reducing fouling and breaking up agglomerations; the backmixed recirculating liquid may lead to growth of larger crystals, as recirculating crystals contact supersaturated liquid emerging from the mixer 12. These arrangements provide a back mixed environment suitable for the promotion of crystal growth.

Referring now to FIG. 6 there is shown an alternative modification to the apparatus 10 of FIG. 1 (that would be equally applicable to the apparatus of FIG. 4) in which an ultrasonic transducer 44 is mounted on the outside of the end wall of the vortex chamber 14 of the fluidic vortex mixer 12. This is particularly suitable with a vortex mixer 12 of diameter above say 20 mm; for example the vortex mixer 12 in this embodiment might be of internal diameter 50 mm. As with the crystallisation apparatus 10 of FIG. 1, during operation the transducer 44 is continuously energised so that the liquid experiences intense insonation as the solution becomes supersaturated. In this embodiment the outflow from the vortex mixer 12 feeds directly into an open-topped holding vessel 46 including a stirrer 47 and with an array of ultrasonic transducers 48 attached to its wall. It will be appreciated that if the crystal growth process is slow the outlet from the vessel 46 may be supplied to a pulsed flow reactor comprising linked vortex cells in which a pulsed flow ensures a well-defined residence time, as described in GB 2 242 376 B or as described in WO 00/29545; as in the holding vessel 46, each vortex cell in such a pulsed flow reactor may be supplied with wall-mounted transducers to suppress agglomeration and prevent fouling. Such transducers may be energized continuously to encourage formation of small crystals, or in short bursts intermittently where larger crystals are required.

In an alternative mode of operation, if the enhanced nucleation is not required, then the transducer 44 might be energized only if fouling occurs within the vortex mixer 12. The presence of such fouling may be detected by measuring the pressure drop between the inlet and outlet of the mixer 12.

In the examples above, the mixture of liquids and crystals generated in the fluidic vortex mixer 12 is fed into a receiver vessel 24, 28 or 46 in which the crystal growth process is completed, ultrasonic irradiation preventing crystal agglomeration during this stage. The crystals initially formed in the mixture are small, and have a narrow size distribution. There is a risk that crystal ripening may occur in the receiver vessel, with the larger crystals growing at the expense of the smaller crystals, which re-dissolve. It may therefore be preferable to omit the receiver vessel 24, 28 or 46, and instead to spray the mixture to form an aerosol. The droplets in the aerosol can then be dried to form a powder of small crystals.

The fluidic vortex mixer may differ from that described above, for example having a chamber of diameter 8 mm, with a conical recess in one end wall leading to an axial outlet of diameter 0.8 mm, and with three equally-spaced tangential inlets around the periphery. As in FIG. 6, a transducer 44 (of frequency say 50 kHz) is attached to the other end wall of the chamber. The solution S and the anti-solvent A are supplied to two of the tangential inlets, while a gas such as compressed air is supplied to the third tangential index. The resulting spray forms an aerosol that can be dried.

Figure 7:
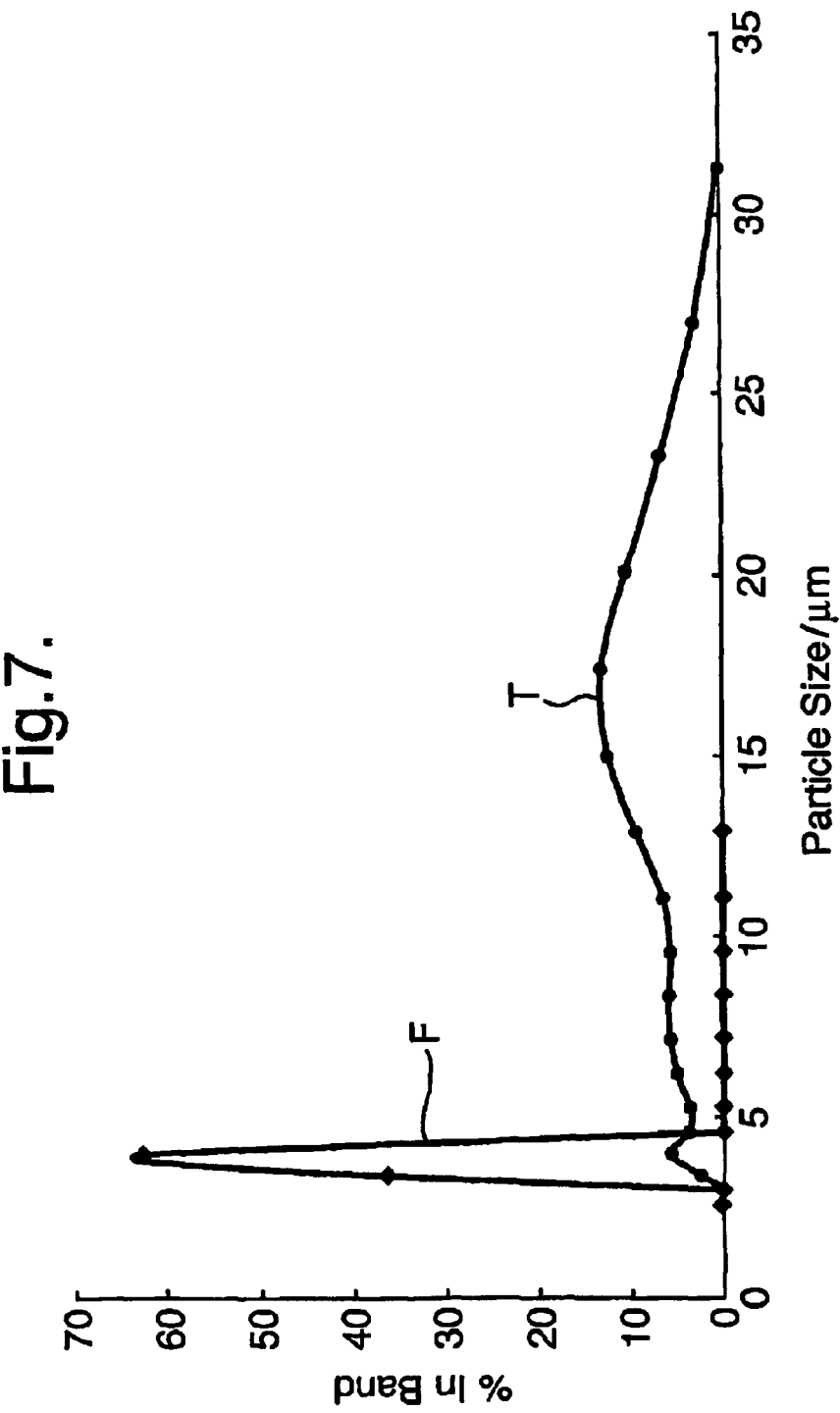
FIG. 7 shows particle size distributions for crystals made in two different ways.

Referring now to FIG. 7, the crystal size distribution (marked F) is shown for crystals of a pharmaceutical product driven out of solution by an anti-solvent (drowning out crystallisation), using such a fluidic vortex mixer. For comparison the size distribution obtained with a stirred tank reactor is also shown, marked T. In the case of the fluidic mixer, crystals were trapped onto a filter paper using a vacuum pump from the spray emerging from the vortex mixer, to provide a sample. It will be observed that the fluidic vortex mixer gives a very narrow size distribution (about 3.0–4.5 $\mu$m), whereas the stirred tank gives a far broader size spectrum (about 3 $\mu$m to 30 $\mu$m).

Referring now to FIG. 8 a crystallisation apparatus 50 is shown with some similarities to that of FIG. 6. A vortex mixer 12 carries an externally mounted ultrasonic transducer 44. A hot saturated solution S of a material whose solubility increases with temperature is supplied to the vortex mixer 12. In this example the anti-solvent A is a compressed inert gas (such as nitrogen). The outlet from the vortex mixer 12 feeds into a closed separation chamber 52 with an outlet 53 at its base for a suspension of crystals in liquid, and an outlet 54 near the top for gas and solvent vapour. The outlet 54 communicates via a compressor 56 to a high-pressure storage vessel 58 from which the compressed gas is fed into the vortex mixer 12. Solvent vapour that condenses in the vessel 58 may be recycled. The mixer 12 is designed to operate with a significant pressure drop so that the inert gas expands and cools (as a result of the Joule-Thompson effect). Cooling also occurs as a result of evaporation of solvent into the gas. The combination of cooling and increasing concentration rapidly generates a supersaturated solution, while the application of ultrasound from the transducer 44 promotes crystal nucleation in a uniform and controlled manner. Ultrasonic transducers 26 are preferably also mounted upon the walls of the separation chamber 52 to suppress agglomeration and prevent fouling.

In a modification to the apparatus of FIG. 8, the vortex mixer 12 on which the transducer 44 is mounted, and to which a saturated solution and an anti-solvent are supplied, sprays the mixture directly into a spray dryer. In the spray dryer the droplets containing crystals are contacted by a stream of hot gas, so both the anti-solvent and the solvent evaporate. Hence a fine solid product is produced. Ultrasonic transducers may be mounted on the walls of the spray dryer to generate ultrasonic waves in the gas, to prevent the fine particles from agglomerating.

It should be appreciated that a crystallisation apparatus of the invention may differ from those described above. In particular the frequency of the ultrasonic transducers may be in the range say 20 kHz to 1 MHz. Where the transducer probe projects through a wall into the vortex chamber (as in FIG. 1), the frequency is desirably selected in accordance with the dimensions of the cell and of the probe so the probe is sealed to the wall at a nodal point. If, as in FIG. 6, the ultrasonic transducer is coupled to the outside of the wall of the vortex chamber, it will be appreciated that instead one or more transducers might be coupled to the curved side wall of the vortex chamber rather than to the flat end wall; this is more appropriate for larger vortex chambers of height in excess of 15 mm.

It will also be understood that a crystallisation apparatus of the invention may be suitable for use in crystallising a wide variety of different compounds. Some materials for which this crystallisation procedure and apparatus would be useful, in order to provide a narrow particle size distribution and so to help control bio-availability, are: analgesics such as codeine; anti-allergens such as sodium cromoglycate; antibiotics such as penicillin, cephalosporins, streptomycins, or sulphonamides; antihistamines; anti-inflammatories; bronchodilators; or therapeutic proteins and peptides. This list is not intended to be exhaustive, as the invention is applicable to substantially any crystallisation process. Other possible compounds would be amino-alcohols, pectins, and complex sugars. Other contexts in which the size distribution and mean size of particles and their morphology are important to the use of the material include dyes and pigments such as azo compounds, and photo-chromatic compounds, and the production of some catalyst materials.

For example potassium penicillin G may be precipitated from solution in n-butyl acetate using an alkaline anti-solvent such as potassium hydroxide or potassium acetate solution. A further benefit in this case is that the intense mixing in the presence of ultrasound inhibits the creation of localized regions of high-pH, in which the base-catalysed formation of the impurity penicilloic acid may occur. The more uniform size distribution is desirable in this case, as is the suppression of fouling.

As another example, a range of different amino acids and proteins may be precipitated. For example pectins can be precipitated from an aqueous solution using an ethanol anti-solvent, and possibly also adjustment of pH. Complex sugars such as glucosamine may also be precipitated, in this case the crystallisation preferably being performed primarily by cooling, for example using an apparatus as described in FIG. 8 in which the anti-solvent is an inert gas such as nitrogen arranged to cause cooling of the solution. Other sugar-related compounds such d-maltose, sucrose, and d-cellobiose can be crystallised in a similar way: these compounds dissolve in hot water, but do not readily crystallise when cooled (a saturated solution at 50° C. will not form crystals even when cooled to 20° C. and left for 24 hours), but form small crystals in the presence of ultrasound, for example with the apparatus as in FIG. 8.

What is claimed is:

1. A method of performing crystallization in which fluids are mixed to cause precipitation or crystallization by passage through a fluidic vortex mixer, wherein the residence time of the fluids in the fluidic vortex mixer is less than 0.5 s, and wherein the fluids within the fluidic vortex mixer are subjected to high intensity ultrasound at an intensity greater than 0.3 W/cm$^2$.

2. A method as claimed in claim 1. wherein the residence time of the fluids in the fluidic vortex mixer is lees than 0.1 s.

3. A method as claimed in claim 1. wherein the ultrasound is supplied by a probe extending into the vortex chamber of the fluidic vortex mixer.

4. A method as claimed in claim 1 wherein an ultrasonic transducer is coupled to a wall of the vortex chamber so that ultrasound is transmitted through the wall into the vortex chamber.

5. A method as claimed in claim 1 wherein ultrasonic transducers are arranged to subject the liquid strewn, supplied to the vortex mixer, to ultrasonic insonation in such a way that ultrasound propagates through the fluids and pipes carrying those fluids into the vortex mixer.

6. A method of performing crystallization in which fluids are mixed to cause precipitation or crystallization by passage through a fluidic vortex mixer, wherein the residence time of the fluids in the fluidic vortex mixer is less than 0.5 s, and wherein the fluids within the fluidic vortex mixer are subjected to high intensity ultrasound at am intensity greater than 0.3 W/cm$^2$ wherein at least two of the fluids that are mixed are liquids, and a gas is also mixed with the fluids within the fluidic vortex mixer.

7. A method of performing crystallization in which fluids are mixed to cause precipitation or crystallization by passage through a fluidic vortex mixer, wherein the residence time of the fluids in the fluidic vortex mixer is less than 0.5 s, and wherein the fluids within the fluidic vortex mixer are subjected to high intensity ultrasound at an intensity greater than 0.3 W/cm$^2$ wherein the fluids emerging from the fluidic vortex mixer comprise a liquid and are sprayed into a drying zone.

8. An apparatus for mixing two fluids, the apparatus comprising a fluidic vortex mixer comprising a substantially cylindrical vortex chamber with at least two peripheral inlet ducts at least one of which is substantially tangential, and with an axial outlet duct, and containing no baffles to disrupt the vortex flow, to enable rapid and thorough mixing of the fluids, and also comprising means to subject the fluids within the vortex chamber to high-intensity ultrasound.

9. An apparatus as claimed in claim 8 wherein the ultrasonic means comprises a probe extending into the vortex chamber of the fluidic vortex mixer.

10. An apparatus as claimed in claim 8 wherein the ultrasonic means comprises a transducer coupled to a wall of the vortex chamber so that ultrasound is transmitted through tile wall into the vortex chamber.

11. An apparatus am claimed in claim 8 wherein the ultrasonic means comprises ultrasonic transducers arranged to subject the fluid streams supplied to the vortex mixer to ultrasonic insonation in such a way that ultrasound propagates through the fluids and pipes carrying those fluids into the vortex mixer.

12. A method as claimed in claim 1 wherein ultrasonic transducers are arranged to subject the fluid mixture emerging from the vortex mixer to ultrasonic insonation in such a way that ultrasound propagates through the fluids and pipes carrying those fluids from the vortex mixer.

* * * * *